United States Patent [19]

Finley et al.

[11] Patent Number: 4,514,681
[45] Date of Patent: Apr. 30, 1985

[54] FLUSH ELECTRICAL RESISTANCE CORROSION PROBE

[75] Inventors: Charles M. Finley; Clifford G. Moore, both of Arcadia, Calif.

[73] Assignee: Rohrback Corporation, Santa Fe Springs, Calif.

[21] Appl. No.: 486,108

[22] Filed: Apr. 18, 1983

Related U.S. Application Data

[63] Continuation-in-part of Ser. No. 447,611, Dec. 7, 1982, abandoned.

[51] Int. Cl.³ ............................................. G01R 27/02
[52] U.S. Cl. .................................................. 324/65 CR
[58] Field of Search .................. 338/13; 73/27, 86; 324/65 CR

[56] References Cited

U.S. PATENT DOCUMENTS

| | | | |
|---|---|---|---|
| 2,735,754 | 0/0000 | Dravnieks | 23/230 |
| 2,851,570 | 9/1958 | Schaschl | 201/63 |
| 2,994,219 | 8/1961 | Schaschl | 73/86 |
| 3,015,950 | 1/1962 | Doctor et al. | 73/86 |
| 3,320,570 | 5/1967 | Lied, Jr. | 338/13 |
| 3,846,795 | 11/1974 | Jones | 340/421 |
| 3,854,087 | 12/1974 | Frenck et al. | 324/65 |
| 3,910,830 | 10/1975 | Mayse | 204/195 |
| 3,936,737 | 2/1976 | Jeffries, Sr. | 324/65 |
| 3,948,744 | 4/1976 | Cushing | 204/195 |
| 3,980,542 | 9/1976 | Winslow, Jr. | 204/195 |
| 3,996,124 | 12/1976 | Eaton et al. | 204/195 |
| 4,179,653 | 12/1979 | Davies et al. | 324/65 |
| 4,208,264 | 0/0000 | Polak et al. | 204/195 |
| 4,226,693 | 0/0000 | Maes | 204/195 |
| 4,338,563 | 0/0000 | Rhoades et al. | 324/65 |

Primary Examiner—Stanley T. Krawczewicz
Assistant Examiner—Jose M. Solis
Attorney, Agent, or Firm—Gausewitz, Carr, Rothenberg & Edwards

[57] ABSTRACT

An all metal-welded flush electrical resistance probe for measuring corrosion of a fluid in a pipe avoids problems of sealing dissimilar materials by using a thin, metallic test disc that is welded around its periphery to the open end of a probe body which also mounts a reference element. The very thin test element is backed up by a solid supporting medium within the probe body, and resistance of the test disc is measured between a point at the disc periphery and a point nearer to the disc center.

16 Claims, 3 Drawing Figures

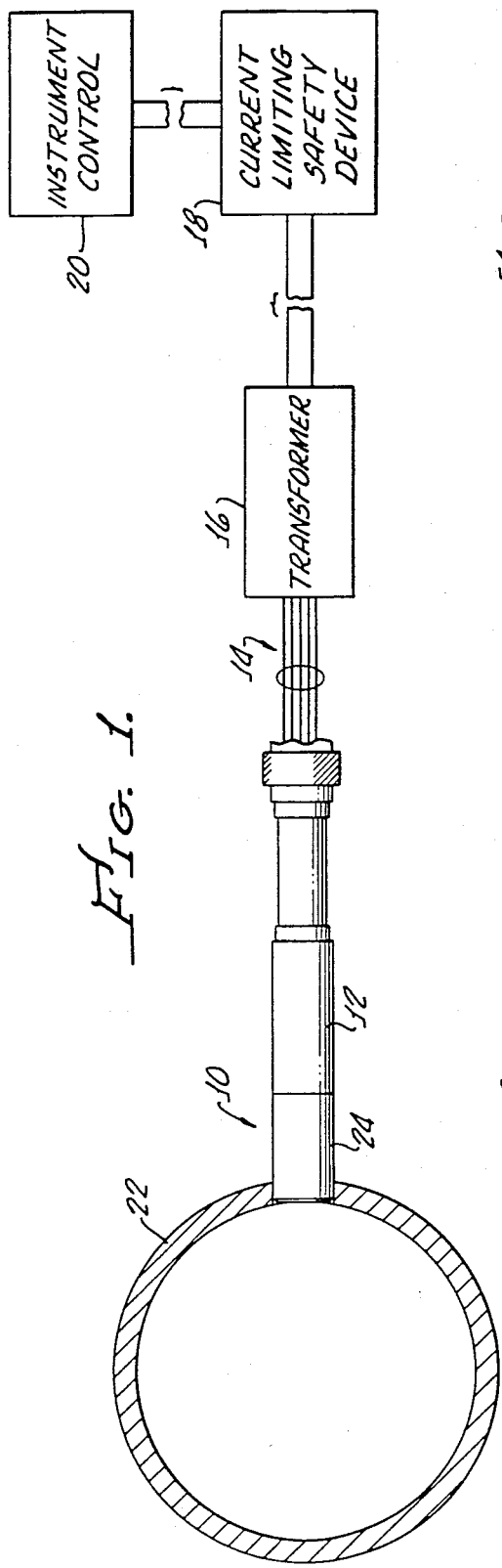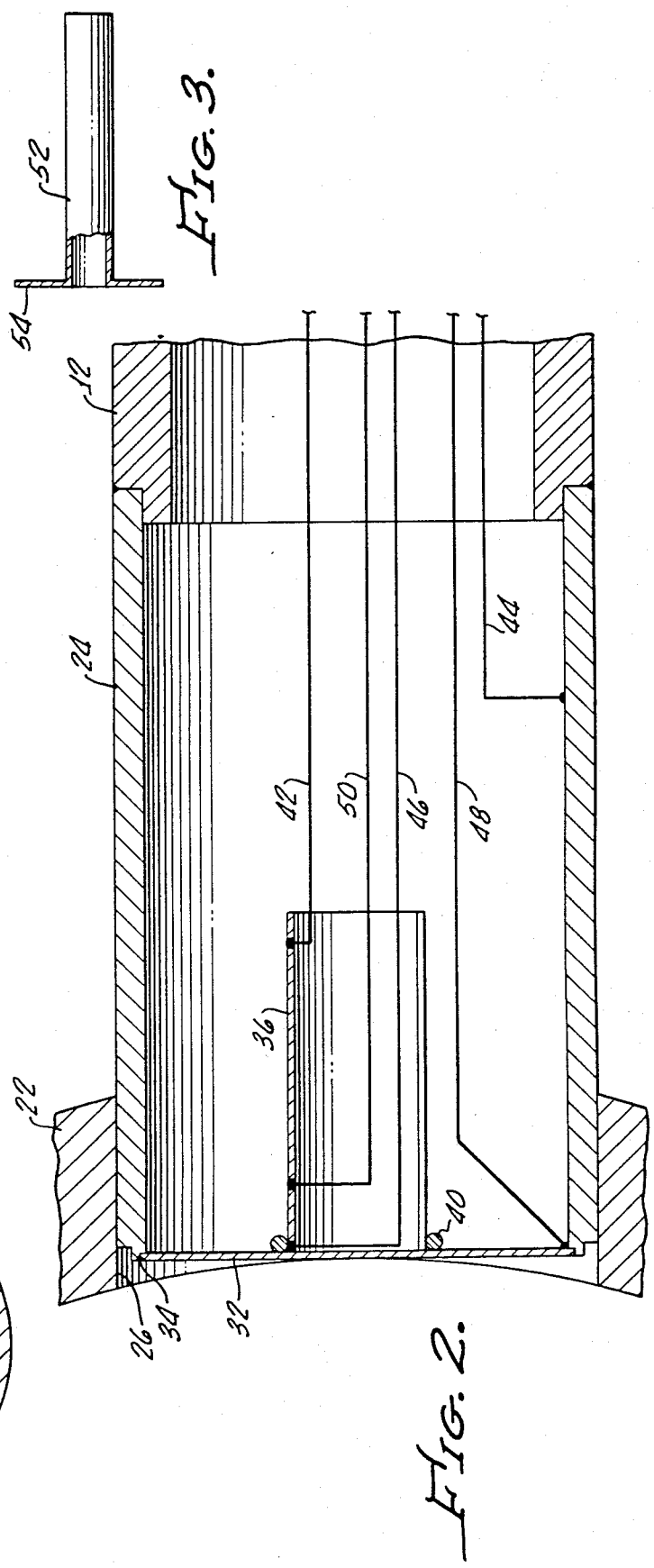

FLUSH ELECTRICAL RESISTANCE CORROSION PROBE

This application is a continuation-in-part of U.S. patent application Ser. No. 447,611, filed Dec. 7, 1982, now abandoned, for FLUSH ELECTRICAL RESISTANCE CORROSION PROBE.

BACKGROUND OF THE INVENTION

The present invention relates to measurement of corrosive characteristics of a fluid and more particularly concerns a corrosion measuring probe that can be mounted flush with the interior of a fluid pipe or container.

A common method of continuous measurement of corrosive characteristics of a fluid employs resistance measurement of a metallic, corrodible test element to indicate, by change of resistance, the amount of metal that has been lost by corrosion over a period of time. A widely used instrument for this measurement is known as a Corrosometer probe manufactured by Rohrback Corporation, assignee of the present application. A probe of this type is described in U.S. Pat. No. 4,338,563 for Corrosion Measurement With Secondary Temperature Compensation, issued to Rex V. Rhoades and James L. Geer. In one form, the probe employs a long, tubular, metallic test element carrying an inner reference element made of the same material as the test element. The interior of the tubular test element is filled with a thermally conductive, electrically nonconductive compound. Alternating current is passed through the elements, and electrical resistance of each is measured while or after the probe has been immersed in an environment of which corrosive tendencies are to be monitored. Because electrical resistance of the metal changes with the amount of metal in the test element, measurement of test element resistance provides an indication of corrosion. Because electrical resistance of the metal also changes with temperature, a reference element is provided made of the same material as the test element and having the same temperature resistance characteristic. Therefore, changes in resistance of the test element that are due to long term temperature variation are eliminated by comparison of resistances of the test and reference elements.

Long tubular probes of the type shown in U.S. Pat. No. 4,338,563 are generally used by immersion in the fluid of which corrosive tendencies are to be sensed, and the entire exterior surface of a part of the tubular probe acts as the test element. Such a probe is not nearly as suitable for measurement of fluid flowing in pipe, and, in such applications, it is preferred to use a probe having a sensing or test element that is substantially flush with the interior surface of the pipe. A flush probe will minimize disturbance to fluid flow caused by the measurement and will provide more reliable corrosion measurement. One type of such flush probe includes a probe body that extends through a pipe wall and has an end that is flush with the pipe interior. The end of the body is filled with a nonconductive insulating and sealing glass, and a metallic ribbon of a test material is mounted on the end of the glass and has electrically conductive end portions extending through the glass end seal to the interior of the probe body. Such a probe is useful only with a small number of special metals, if the probe must be employed over a wide temperature range as is commonly required. In pipelines and chemical plants, corrosive fluid temperatures may be in the order of 400° F. to 500° F. At such temperatures the great difference in the coefficient of linear expansion between the metal of the test ribbon and the glass of the seal frequently breaks the seal and thus prevents any extended life for such a probe. Glass seal flush probes are not sufficiently reliable nor rugged enough, and at least partly for this reason, flush probes are not as widely used as they might be. If more reliable and rugged flush probes were available, their use would be significantly increased.

Accordingly, it is an object of the present invention to provide a flush corrosion resistance probe that avoids or eliminates above-mentioned problems.

SUMMARY OF THE INVENTION

In carrying out principles of the present invention in accordance with a preferred embodiment thereof, a flush electrical resistance corrosion probe includes an elongated tubular probe body and an electrically conductive corrosion test membrane extending across and sealing the open end of the body. The membrane has a thickness considerably less than the thickness of the probe body wall, and a reference element is mounted within the probe body, which is filled with a supportive material, such as a thermally conductive and electrically nonconductive solidified cement. Acording to a feature of the invention, the corrosion test membrane comprises a thin metal disc that is continuously welded around its periphery to the end of the probe body and is arranged to be positioned flush with the interior surface of a pipe. Resistance of the test element is measured between a point near its periphery and a point closer to its center. According to another feature of the invention, the test and reference elements are integral with one another, being made from a unitary piece of metal.

BRIEF DESCRIPTION OF THE DRAWINGS

FIG. 1 illustrates a corrosion measuring probe embodying principles of the present invention, installed for corrosion measurement of a fluid flowing within a pipe;

FIG. 2 is an enlarged sectional view of parts of the probe of FIG. 1 showing details of its construction and relation to the wall of a pipe in which it is installed; and FIG. 3 shows integral test and reference elements that may be used in the probe of FIG. 2.

DETAILED DESCRIPTION OF THE INVENTION

As shown in FIG. 1, a probe, generally indicated at 10, is mounted to an adapter 12, which carries a plurality of electrical conductors 14 connected through a transformer 16 and current limiting safety device 18 to an instrument control and readout device 20. Probe 10 is mounted in any well known and suitable manner within an opening formed in the wall of a pipe 22 through which flow fluids of which corrosive tendencies are to be measured. A conventional sealing connection between the exterior of the probe 10 and the aperture in the wall of pipe 22 is provided, as is well known.

Details of the probe structure are illustrated in FIG. 2 which shows a probe body 24 formed of a tubular cylinder of steel, or like metal, having a wall thickness of approximately five hundredths of an inch. The forward end of probe body 24 is mounted within and sealed to an aperture 26 formed through the wall of the pipe 22 so that the forward end of the probe body is substantially flush with the interior of the pipe. The forward end of the probe body is formed with an inwardly facing circumferential shoulder 30 upon which is seated a metal diaphragm or thin test disc 32, also made of steel or similar metal. Test disc 32 is made with a thickness considerably less than that of the probe body, a thickness in the order of ten mils, for example, so as to provide a suitably sensitive corrosion reading. Corrosion is indicated by the electrical resistance of the disc, which, in turn, is related to the disc thickness. As the test disc is corroded by the environment to which it is exposed, its thickness decreases and, accordingly, its electrical resistance increases to provide an indication of the amount of corrosion. The test element must be extremely thin in order to provide increased sensitivity. The thinner the test disc, the greater the change in increased electrical resistance for a given amount of corrosion. Test disc 32 not only provides a large area of test material exposed to the corrosion environment, but itself seals the interior of the probe body. The disc is continuously welded about its periphery to the forward end of the probe body by means of a continuous weld, indicated at 34, to provide a rugged and reliable seal.

A tubular reference element 36 made of the same material as test disc 32 and open at both ends is welded, as indicated at 40, at its forward end to a central portion of the inner surface of the test disc 32. The reference element 36 may be made of a thicker material that is more easily handled, as it is not exposed to the corrosive environment and, therefore, is not subject to corrosion and electrical resistance changes. Electrical leads or conductors 42 and 44 are connected, respectively, to an inner end of the reference element 36 and to an inner portion of the probe body 24. These leads are connected via the conductors 14, transformer 16 and current limiting safety device 18 to a source of power that causes current to flow through both the reference element and the test disc. Measurement of resistance of the test disc 32 is made by means of a pair of leads 46, 48, of which lead 46 is connected to the junction of the forward end of the reference element and the test disc at a point near the center of the test disc, whereas lead 48 is connected to the test disc at a point adjacent its outer periphery, where it is welded to the forward end of the probe body.

Measurement of the resistance of the reference element 36 is made by means of lead 46, which is connected to both the test disc and the forward end of the reference element, and by an additional lead 50 connected to the reference element at an inner portion thereof.

The inner or rearward end of probe body 24 is fixedly connected to the adapter 12 which contains the electrical conductors and suitable connections for connecting the conductors to the instrument control.

The interior of the probe body and the interior of the reference element are filled with a thermally conductive, electrically nonconductive solid supportive material which contacts all of the interior surface of the thin test disc 32 and provides solid structural support for this very thin test element.

In the probe configuration of FIG. 2, one may encounter problems, due to the difficulty of obtaining a continuously uniform weld 40 around the junction of the reference element 36 and test element 32. This difference may be due, at least in part, to the different sizes or thickness of the materials and, in particular, to the difficulty of welding the extremely thin material of the test disc 32. Nonuniformity of the weld 40 between the test and reference elements may give rise to undesirable nonlinearities in the measurement.

It will be noted that the resistance of the test element 32 is measured by flowing current in an essentially radial path between the outer perimeter of the test disc and the junction of the test disc with the reference element. This junction, at weld 40, accordingly carries the highest current, and precision measurement of corrosion requires the same resistance around the entire periphery of the reference element at its junction with the test element. This is so for the following reason: The test element itself may not corrode uniformly over its entire surface, due to various conditions that may exist in the corrosive environment. Thus, there may be pitting of the test element, and measurement of corrosion due to a pit at one point may be different than measurement of corrosion due to an essentially similar pit at another point, if the electrical resistance of the weld 40 varies in the current paths that include the pitted areas. Corrosion may also vary because of flow dynamics. For example, the leading edge of the test disc 32 (that is, the edge of the test disc that is upstream) may experience a greater corrosion than a downstream portion of the test disc, and, thus, a nonuniform resistance around the perimeter of the test element, namely, at weld 40, may cause different measurements for different corroded areas of the test disc.

The arrangement of FIG. 3 substantially eliminates this cause of measurement nonlinearity. In the arrangement of FIG. 3, the test and reference elements are made integral with one another. A short length of circular cross-section steel bar stock is machined to provide a solid or hollow reference element 52 having integrally formed thereon at one end a thin test disc element 54. The bar stock from which the unitary structure of test and reference elements is made may be a section of three quarters of an inch in diameter and one and a half inches in length. The reference element 52 may be machined or turned down to a diameter of a quarter inch, with the disc element 54 integrally attached to one end of the reference element having the original three quarter inch diameter, but having a thickness of about ten mils.

Preferably, the integral reference element is made hollow, as by drilling out the center of the solid element after turning down the outside of the bar stock to form the integral test disc element. The hollow configuration reduces thermal capacity, and thus provides a faster transient response time and less thermal lag in the presence of thermal variations. Having less thermal mass in the reference element, there is less steady state error due to thermal gradient between the environment being tested and the reference element. Moreover, the hollow reference element presents a greater electrical resistance than the solid element and is less sensitive to location. The electrical lead to the reference element is connected to this element at a point closer to the test element, and thus further decreases thermal lag.

This construction surprisingly and unexpectedly provides a number of improved results. The difficult procedure of welding a separate test disc to a reference element is entirely eliminated, and, thus, uniformity of resistance at the junction of test and reference elements is maximized to thereby minimize nonlinearities of corrosion measurement at different points of the test disc. The unitary and integral configuration of test and reference elements also eliminates thermocouples that may be generated by use of dissimilar metals for these elements or which may be generated to some degree even by different pieces of the same metal and, furthermore, provides the best thermal compensation by ensuring use of the same materials for both test and reference elements. There is no possibility with this arrangement that test and reference elements may be made of different materials or of different pieces of similar materials, as may possibly occur through accident, mishandling or failure to identify the several parts when individually made.

The combined test and reference element structure of FIG. 3 is mounted in the probe body in the same manner as are the corresponding components of the probe of FIG. 2. The interior of the probe body and the interior of the hollow reference element are filled with thermally conductive, electrically nonconductive solid supporting material to contact all of the interior surface of the thin test disc to provide solid structural support therefor. Furthermore, the leads, such as leads 42, 46, and 50, are connected to the exterior of the solid reference element body 52, but otherwise the probe is constructed and operates in the same manner as described in connection with the embodiment of FIG. 2.

The described probe provides a significantly greater area of exposed test element than prior flush probes. For example, a ribbon-type flush probe, wherein a metallic ribbon has ends extending through a glass seal, will provide a metallic test ribbon three eighths of an inch long by three sixteenths of an inch in width, whereas a typical test disc used in the probe described herein may have a diameter in the order of three quarters of an inch. Thus, the area of the test disc that is exposed to the corrosive fluid between the connections of resistance measuring conductors 46 and 48 is significantly increased. Increased area enhances the accuracy of the corrosion measurement.

The described probe enables flush mounting of the probe end in substantial alignment with the interior surface of a pipe or container wall. It provides a test element of a suitably large area, and, importantly, eliminates the problem of sealing and maintaining a seal between dissimilar materials over a wide range of temperatures. The embodiment of FIG. 3 significantly improves probe performance in several respects, including avoidance of unwanted thermocouples, better thermal compensation, and better linearity of measurement.

The foregoing detailed description is to be clearly understood as given by way of illustration and example only, the spirit and scope of this invention being limited solely by the appended claims.

What is claimed is:

1. A flush electrical resistance corrosion probe comprising
   an elongated tubular probe body having an outer wall and an open forward end,
   an electrically conductive corrosion test membrane extending across and sealing said open end, said test membrane having a thickness considerably less than the thickness of said probe body wall,
   a reference element mounted within said probe body,
   means for measuring resistance of said test membrane including first and second electrical conductors connected to first and second points on said test element, and
   a thermally conductive and electrically nonconductive support material in said probe body in supportive contact with said test membrane.

2. The probe of claim 1 wherein said test membrane comprises a thin metal disc welded along its periphery to the forward end of said probe body wall.

3. The probe of claim 2 wherein one of said conductors is connected to said disc near the center of said disc.

4. The probe of claim 2 wherein said conductors are connected to points at the periphery and near the center of said disc.

5. The probe of claim 2 wherein said reference element is connected to said disc within said probe body and spaced from said probe body wall, and wherein one of said conductors is connected to both said disc and said reference element.

6. The probe of claim 2 wherein said disc has a thickness of about ten mils.

7. The probe of claim 1 wherein said reference element and test membrane are integral with one another.

8. The probe of claim 1 wherein said reference element and test membrane are fabricated as a unitary structure from a single piece of material.

9. The probe of claim 1 wherein said reference element comprises a metal cylinder and wherein said test membrane comprises a thin disc integral with one end of said reference element cylinder.

10. The probe of claim 9 wherein said disc has a thickness in the order of about ten mils.

11. The probe of claim 9 wherein said disc is welded along its periphery to said probe body wall.

12. The probe of claim 1 wherein said reference element comprises a hollow metal cylinder integral with said test membrane.

13. A flush electrical resistance corrosion probe adapted to be inserted into a pipe through which flows a corrosive fluid and to present to such fluid a corrosion test element that is substantially flush with the interior of the pipe, said probe comprising
   a tubular probe body having a relatively thick metal wall open at a forward end, said body being adapted to be inserted through an opening in the wall of a pipe with said forward end substantially flush with the interior of said pipe,
   a corrosion test disc seated on said probe body forward end and welded thereto about the periphery of the disc to seal the interior of said probe body, said disc having a thickness much less than the thickness of said probe body wall,
   a reference element within said probe body and fixed at one end to said test disc at points spaced from said probe body wall,
   means for passing current through said test disc and reference element,
   means for measuring resistance of said reference element,
   means for measuring electrical resistance of said test disc comprising a first conductor connected to the disc at a point adjacent its connection to said probe body wall and a second conductor connected to the disc at a point adjacent its connection to said reference element, and
   a thermally conductive support medium within said probe body in contact with said reference element and said test disc and providing structural support for said disc.

14. The probe of claim 13 wherein said probe body forward end is formed with an inwardly facing circumferential shoulder, said test disc being seated upon said shoulder and continuously welded and sealed thereto to seal the interior of the probe body.

15. The probe of claim 13 wherein said reference element and test disc are fabricated as a unitary structure from a single piece of material.

16. The probe of claim 13 wherein said reference element comprises a metal cylinder and wherein said test disc comprises a thin disc integral with one end of said reference element cylinder.

* * * * *